United States Patent [19]

Fisher et al.

[11] Patent Number: 4,888,948
[45] Date of Patent: Dec. 26, 1989

[54] MONITORING OF FOREIGN OBJECT INGESTION IN ENGINES

[75] Inventors: Celia E. Fisher, Southampton; Roy Forfitt, Whiteparish, both of United Kingdom

[73] Assignee: Stewart Hughes Limited, United Kingdom

[21] Appl. No.: 171,683

[22] Filed: Mar. 22, 1988

[30] Foreign Application Priority Data

Mar. 25, 1987 [GB] United Kingdom ............... 8707187

[51] Int. Cl.⁴ .............................................. F02C 7/05
[52] U.S. Cl. .................................. 60/223; 60/39.092; 324/454
[58] Field of Search ............. 60/39.091, 39.092, 39.33, 60/223; 415/118; 324/71.1, 452, 454

[56] References Cited

U.S. PATENT DOCUMENTS

| | | | |
|---|---|---|---|
| 2,994,035 | 7/1961 | Feifel et al. | 324/71.1 |
| 3,784,902 | 1/1974 | Huber | 324/454 |
| 4,312,180 | 1/1982 | Reif et al. | 60/39.091 |
| 4,607,228 | 8/1986 | Reif | 324/454 |
| 4,631,482 | 12/1986 | Newton et al. | 324/454 |

Primary Examiner—Louis J. Casaregola
Attorney, Agent, or Firm—Ostrolenk, Faber, Gerb & Soffen

[57] ABSTRACT

The invention described in this specification relates to apparatus for monitoring the intake of foreign bodies and objects into an engine, particularly a gas turbine engine whereby sensors are located at or near the engine intake for detecting any electrostatic charge induced on the sensors by the passage of foreign bodies therepast. The specification particularly discloses an arrangement for a gas turbine engine in which sensors are provided in the exhaust duct and in the inlet duct and that signals from sensors in the inlet duct and exhaust duct are compared and contrasted.

9 Claims, 8 Drawing Sheets

PULSE OUTPUT    CHARGE OUTPUT

MONITORING EQUIPMENT FOR ENGINE TEST

MONITORING OF FOREIGN OBJECT INGESTION IN ENGINES

DESCRIPTION

This invention relates to the monitoring of foreign object ingestion in engines and has particular reference to, although is not exclusively for, the monitoring of foreign object ingestion in gas turbine engines such for example as jet engines.

Our co-pending British Patent Applications Nos. 8702553 and 8620239 describe and claim methods of measuring electrostatic charges in the exhaust gas stream of a gas turbine engine with a view to determining the on-set of faults and degeneration generally of the engine performance. This is achieved by providing a plurality of sensors in the exhaust duct of the engine to give a plurality of signals whereby the time displacement and amplitude variation of the signals are recorded as detected by the various sensors to give an indication of the general area of the engine in which the fault or problem lies and the type of fault which has occured.

These co-pending applications specifically describe ring sensor assemblies comprising a plurality of arcuate plates having an insulating layer of a ceramic material provided on the surface thereof which ceramic surface further carries a conducting layer for the detection of the passage of charged particles within the exhaust duct of the engine.

It will be appreciated that some of the debris sensed in this was in the exhaust gas stream of an engine may well result from material that has been ingested through the air inlet thereto and has thus passed right through the engine. In jet engines the introduction of foreign objects into the air intake can have a catastrophic consequences and it has been known that, for example, metal objects have produced serious structural faults in engines particularly during take-off and landing. Other objects such as small stones and dust, can pass through the engine without significant effect and yet can produce electrostatic signals in the exhaust gas stream.

According to the present invention, there is provided apparatus for monitoring the intake of foreign bodies into an engine which apparatus comprises one or more sensors located at or near the intake of said engine and means for detecting an electrostatic charge induced on said sensors by the passage of foreign bodies therepast.

The means for detecting an electrostatic charge may include means for measuring a rate of change of the charge induced on said sensors. Alternatively, the means for detecting may include means for measuring the magnitude of said charge.

The present invention also includes an engine incorporating sensors and detecting means in accordance with the present invention. In a preferred embodiment of the present invention, the sensors may be formed about intake of an engine and may be a single ring sensor or a plurality of arcuate sensors.

The Applicants have found that debris ingested into the intake of an engine, particularly a jet engine carries an electrostatic charge. This may be monitored on an intake sensor as a single event. Such debris may comprise stones, rivets and other particulate material of a substantial nature in addition to sand, salt, grit and small particles of dirt. All the debris will be sensed to a greater or lesser extent and which will then pass down either through the by-pass duct of a jet engine or through the inner core of the engine to be expelled from the exhaust system.

The apparatus in accordance with the present invention, therefore, may be used also in conjunction with the apparatus forming the subject of copending Applications No. 8620239 and 8702553. In particular, the condition monitoring of a gas turbine engine may be effected by providing one or more sensors at or near the intake of the said engine, one or more sensors in the exhaust of said engine, and for providing means for detecting electrostatic charge induced in each of said sensors and conducting an analysis of the signals thus detected.

In addition to the foregoing, sensors may also be included in the by-pass to detect debris which is ingested into the engine and passes via the by-pass out of the engine as well as that which passes through the high temperature sections of the engine.

The sensors in accordance with the present invention may be arcuate sensors or spot sensors; arcuate sensors may be spaced about ducting within the engine, while spot sensors may be disposed in a staggered ring around an engine ducting or at other convenient places therein.

Two parameters determine the performance of each sensor, these are the length of the sensor within the ducting and the overall surface area. The effect of length on the sensor in the direction of gas flow on signal shape and duration has shown that signal amplitude is related to the sensor surface area and that charged debris sets up a charge field which is long compared to the change when considered in the axial length of the sensor. In consequence, the engine signal duration is not discernable and the axial length of the sensor does not, therefore, appear to effect the frequency response of a sensor within a reasonable range of length. In practical terms it is preferred that the minimum length of any sensor is constrained to approximately 10 mm usually by the problem of providing adequate lead-in connectors. The maximum length of a sensor is limited by the available space and by the considerations of capacitance. The surface area of a sensor should be maximised and the capacitance should be minimised. In practice a compromise has to be achieved as capacitance is proportional to the surface area for any particular dielectric material. In maximising the surface area, therefore, capacitance could increase to an unacceptable level. As a compromise, a nominal value of 50 mm is a preferred maximum length for a sensor in accordance with the present invention. It will be appreciated, therefore, that the selection of different dielectric materials will enable improved sensor construction.

Each sensor in accordance with the invention may comprise an insulating layer, a bonding layer for bonding said insulating layer to a support surface and an conducting layer carried by said insulating layer characterised in that each of the layers is applied by spraying or coating. Where the sensor is to be in a high temperature environment, the insulating layer is a ceramic layer and the spraying or coating may be effected by plasma spraying or flame spraying.

In one aspect of the invention for a high temperature sensor the bonding coat may have a thickness within the range of 0.5 to 1.5 mm, the ceramic layer may have a thickness of 0.5 to 1.6 mm and the conductor coating or layer may have a thickness of 0.01 to 0.05 mm.

In a typical embodiment of a high temperature sensor for use in accordance with the present invention, the bonding layer may comprise a nickel chromium alloy containing 6% of aluminium. The ceramic layer may be selected from magnesium zirconate or a composition containing alumina, titanium oxide, silica and iron oxide. The conducting layer may be selected from, a stainless steel containing 17% by weight of chromium and 12% of nickel together with up to 3.5% of molybdenum and 1.5% of silicon, or may be a nickel layer of 99%+ purity.

Each sensor may be formed directly on the engine casing or in the alternative, may be formed on a support plate adapted to be secured to the engine casing. In a particular embodiment of the present invention the engine casing may be recessed to accommodate the sensor so that the sensor surface follows substantially the internal surface of the engine casing thus providing the minimum interruption or disturbance to the gas flow.

As stated above, it is preferred that the sensors are substantially segmental in which a plurality are circumferentially spaced around ducting within the engine.

For low temperature sensors to be provided in the intakes and by-pass, the geometrical size and type will be much the same as for the high temperature sensors described above. The material, however, will depend on the local operating environment such, for example, as temperature and humidity. At each location it is desirable that the thermal expansion of the material should be matched as closely as possible to ensure that cracking and loss of material by degradation does not occur. At the intake, ambient conditions will be a relatively low temperature with a wide range of relative humidities. The sensor materials, therefore, should not be susceptible to water absorption. The ceramic materials tend to be porous and will not, therefore, be entirely satisfactory for an intake environment. In a particular embodiment of the present invention, a low temperature sensor may comprise an epoxy based insulator with a epoxy conductor layer thereon. The insulating layer may be a pure epoxy resin and conducting layer may be a silver loaded epoxy resin. This may be covered with an insulating layer to effect waterproofing and to protect from impact.

The advantages are that such materials have a minimum distortion due to thermal effects and, therefore, enjoy reduced possibility of damage from interacting within the environmental conditions. They are relatively easy to apply to irregularly shaped area such as intake ducts, and sensor so formed will provide minimum obstruction to flow passed the sensors.

In another aspect of the present invention, data obtained by intake sensors may be compared with other engine and flight data to provide information about any particular ingestion event and also information regarding possible secondary damage.

The means for detecting an induced charge on a sensor will probably be based on a direct measurement of the charge on the debris as this tends to be a more sensitive technique.

Following is a description by way of example only and with reference to the accompanying informal drawings of methods of carrying the invention into effect.

Figure 1:
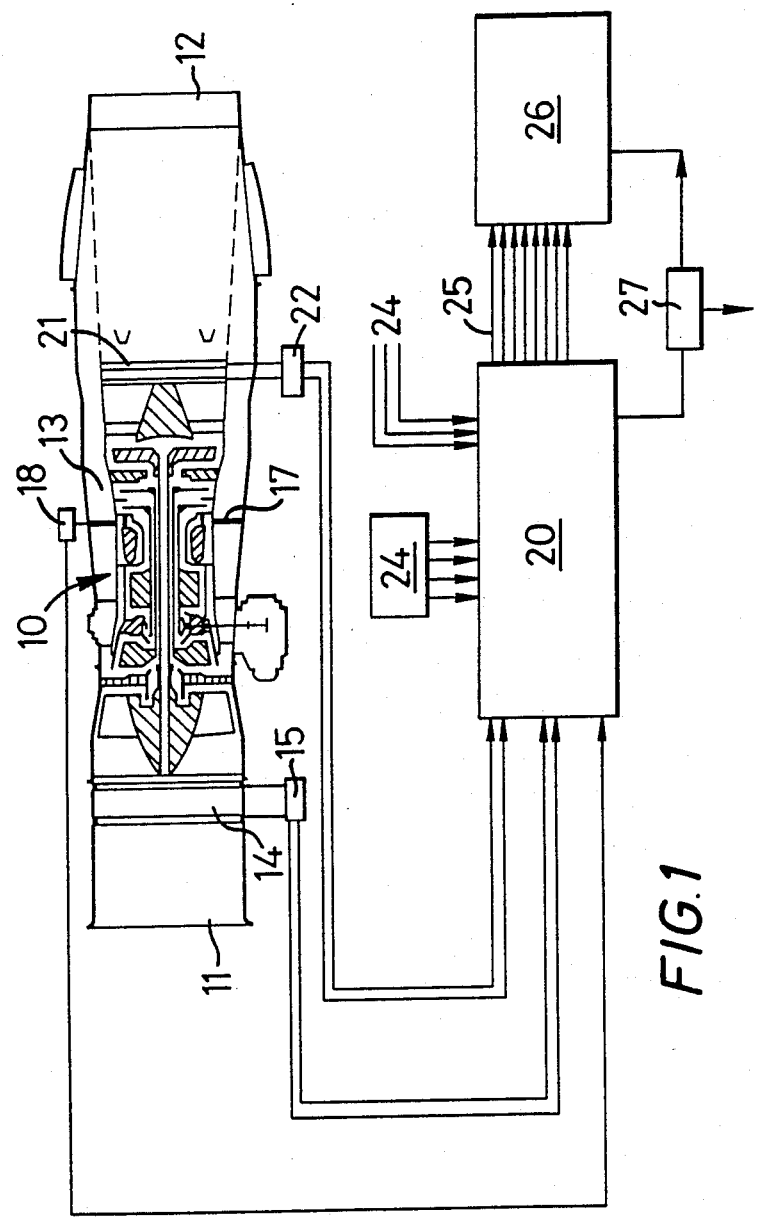
FIG. 1 is a general layout of a foreign object ingestion detection device in operative combination with an exhaust detection device as applied to gas turbine jet engines.

Turning first to FIG. 1, a jet engine indicated generally has an intake 11 and a hot exhaust 12 with a by-pass 13 between intake 11 and exhaust 12.

The intake of the engine comprises a duct having a substantially circular internal surface having a circumferential intake sensor 14 comprising four segmental sensor elements, each of which has been mounted onto the internal surface of the intake duct 11. Each of the segmental sensors comprises an insulating layer of epoxy resin of the order of 0.5 mm thick together with a charge collecting layer applied thereover of silver loaded epoxy resin of approximately 0.05 mm in thickness. Each of the charge collecting layers is provided with an electrical connector comprising a central cylindrical stud having a flanged head adapted to engage the conductive layer of each sensor with the stud passing through the wall of the intaked duct via an insulating grommet for connection to an intake signal conditioning unit indicated generally at 15.

A similar peripheral sensor system 17 is provided within by pass 13 and is coupled to by pass signal conditioning means 18 which is connected to a signal processing station indicated generally at 20.

The exhaust duct 12 carries four segmental sensors 21 circumferentially disposed about the internal surface of the exhaust duct and electrically connected to signal conditioning means 22 which in turn is also connected to signal processor 20. The sensors 21 in the exhaust duct of the engine are in accordance with anyone of Examples 1, 2 or 3 of our co-pending Application No. 8702553.

The signal processing means 20 further has input data 24 from the engine and flight data 24 provided from aircraft flight data from other on board systems.

The signal processor 20 provides a plurality of outputs 25 to an event recorder 26 which records events for subsequent analysis at the completion of the flight regime for the engine. An alarm detector 27 may also be coupled to processor 20 for any significant incidence to be drawn to the attention of the flight crew.

Figure 2:
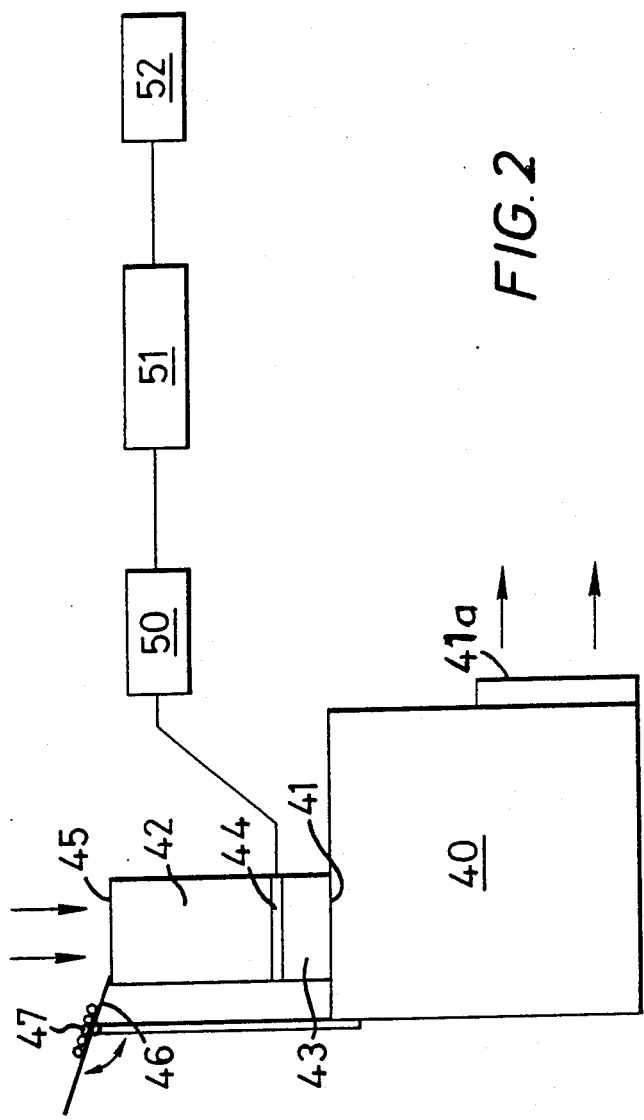
FIG. 2 is a diagram of a laboratory unit for determining the charge of particles passing an intake sensor or probe system.

The feasibility of the techniques in accordance with the present invention depend on the debris passing into the engine being charged. To demonstrate this, a laboratory experiment was conducted using the apparatus illustrated in FIG. 2.

A centrifugal suction rig 40 was disposed with an outwardly directed inlet 41 and a substantially horizontal lower outlet 41a. The inlet 41 was provided with an upstanding cylindrical tube 42 constituting an inlet duct. The tube 42 was provided towards its lower end 43 with an annular ring of circumferential segments 44 disposed on the internal surface and formed by an insulating layer of epoxy resin and a conductive layer of silver loaded epoxy resin of thickness dimensions substantially as described above.

The inlet tube 42 was of substantially 150 mm internal diameter and had a length of approximately 400 mm. The upper end 45 is juxtaposed an inclinable plate 46, the angle of inclination of which can be adjusted. Articles of debris 47 are located on the upper surface of inclined plate 46 and released one at a time or in groups into the inlet end 45 of inlet tube 42.

The fan is capable of producing an air flow within the inlet tube 42 of 12 metres per second. Release of an article of debris 47 into the entrance of the tube results in the article of debris passing substantially centrally of the sensor ring 44 with a velocity approaching 5 metres per second. The sensor ring 44 is coupled to debris detection unit 50 and then via an oscillascope 51 to a chart recorder 52.

Various size small stones ranging from a nominal 2 metres diameter up to a nominal 20 metre diameter were tested individually. To avoid any unintentional precharging of the debris, the metal plate was connected directly to the probe tube, the debris detection unit, the oscillascope and the chart recorder.

Figure 3:
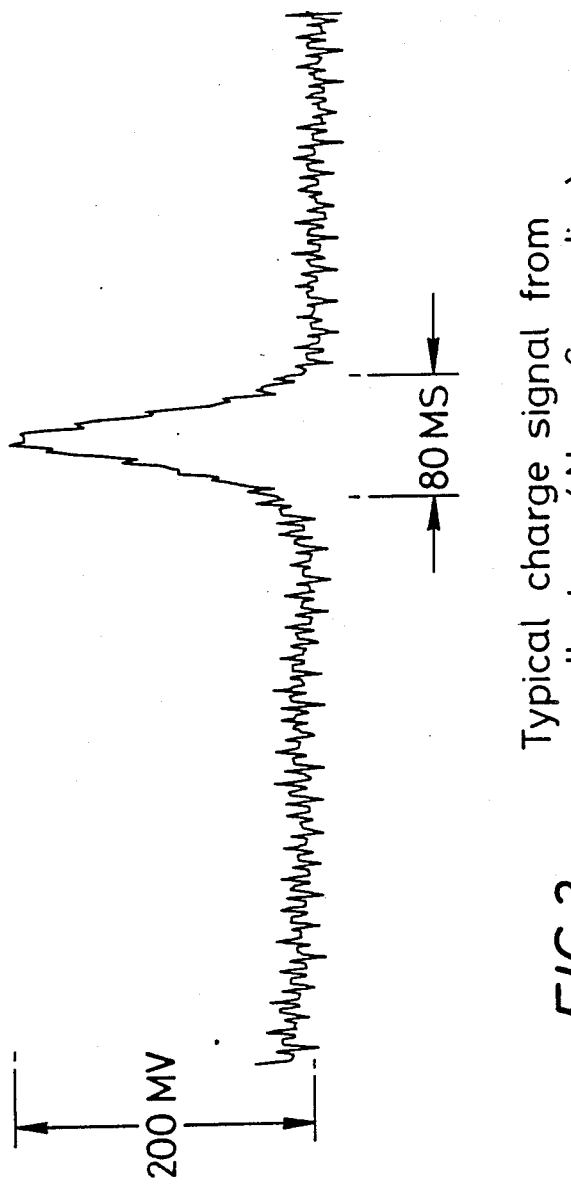
FIG. 3 is a chart showing a typical charge signal from a small stone sensed in the apparatus of FIG. 2.

It was noted that each piece of debris passing the sensor produced an induced charge therein; a typical charge signal is shown in FIG. 3 which is the charge signal for a stone of nominal diameter of 6 mm.

Figure 4:
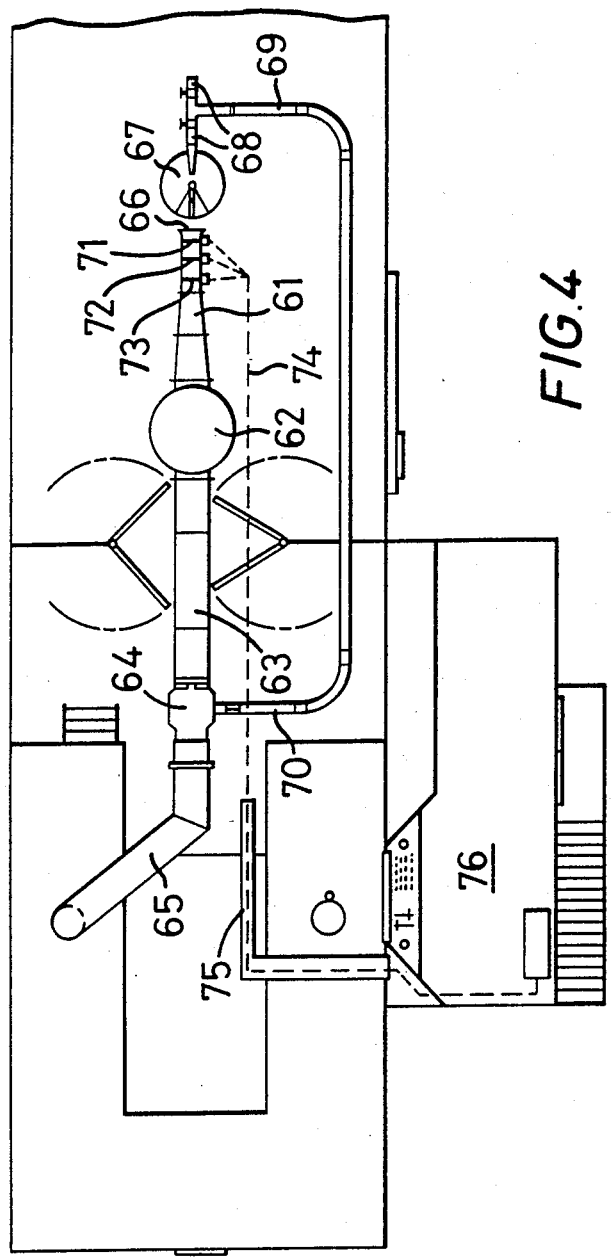
FIG. 4 is a diagram of a simulated engine for sensing the ingestion of foreign objects.

FIG. 4 is test bench arrangement to demonstrate the present invention. The bench comprises an air intake 61 debouching into a debris separator 62. The debris separator is connected with combustor 63 which exhausts into a polouche 64 and debouches into a exhaust 65. The inlet 61 is provided with an inlet mouth 66 in juxtaposition with a turntable assembly 67. A debris accelerator comprises a conduit 68, a branch of which 69 communicates with polouche 64 to provide a by-pass working section 70. The intake 61 is provided with three sensors 71, 72 and 73 each of different construction to enable relative tests on the efficiency of different sensors and materials to be evaluated. The sensors are provided with signal conditioning means juxtaposed each sensor and the condition signals fed by means of conductors 74 passing through cable duct 75 to a control room 76 where the signals are monitored and recorded.

In operation the combustor 63 is ignited by the supply of fuel within the combustion ducts 63. Air is drawn into the system by means of inlet 66 and additional air is drawn through debris accelerator tube 68 and by-pass 69 to reproduce the general conditions within a jet engine.

The turntable assembly is adjustable and enables selected components or solid items to be ingested into the engine and duct to be presented to inlet 66 so that its passage past sensors 71, 72 and 73 may be monitored by means of the signals induced in each of the sensors.

In a particular experiment, sensor 71 comprised an insulated layer of flexible epoxy 25 mm wide, a conducting layer of silver loaded epoxy 13 mm wide and a top insulayer of flexible epoxy 25 mm wide. Sensors 72 and 73 each comprise an insulating layer of flexible polymer material, a conductive layer of silver loaded epoxy and a top insulating layer of a flexible polymer material. The overall dimensions of all three sensors were identical. The lead-out connection to the signal conditioning was effected using a cable which is bonded to the conductive layer employing a conductive epoxy. Individual signal conditioning units are operatively connected with each sensor on the intake working section.

Debris is injected into the intake working section using the turntable assembly to simulators realistically as possible ingestion of the article into a jet engine intake, such as will be caused by the effect of thrust or reverse thrust of a jet engine. Debris is collected in the debris separator to ensure that the test engine is not damaged.

Figure 5:
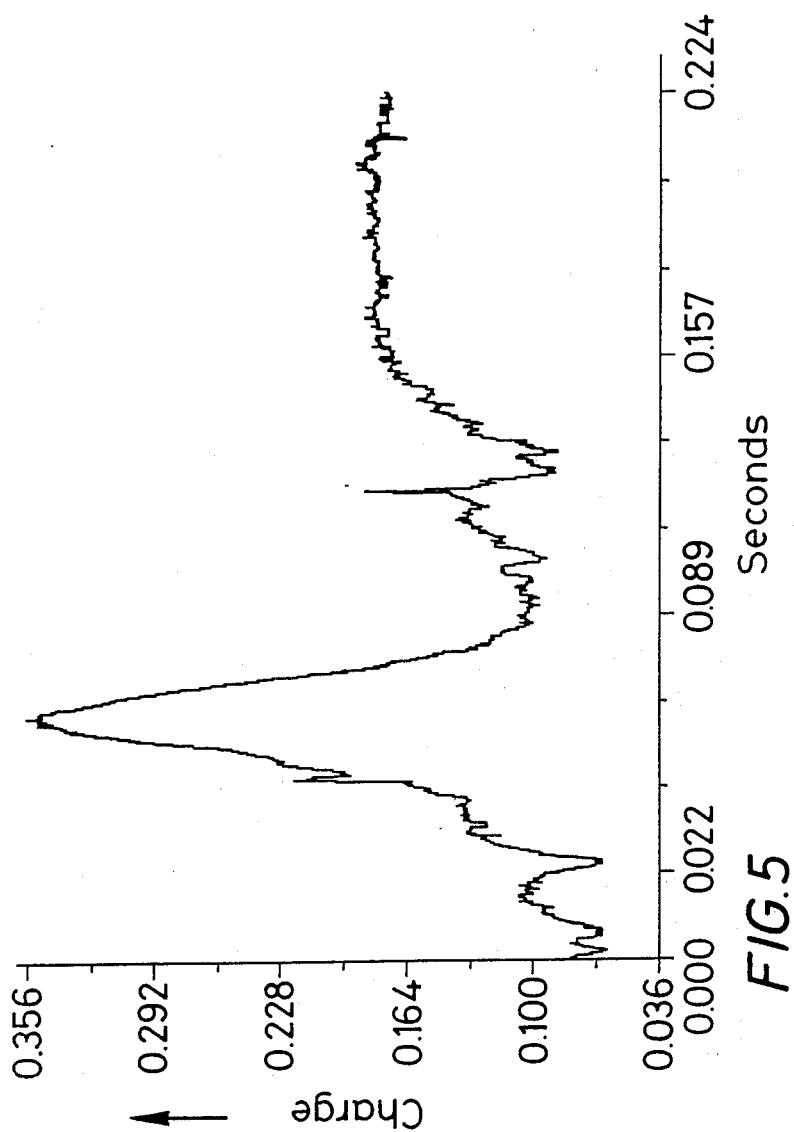
FIG. 5 is a signal trace of an object sensed in the apparatus of FIG. 4.

The accompanying FIG. 5 shows a typical signal from this test facility caused by a bolt passing through the intake section.

From the aforementioned co-pending British patent application No. 8620239 it will be apparent that the sensors of the present invention, i.e. the sensors 14, 17, and 21, could take on a configuration as described below by reference to FIGS. 6–9. Similarly, the aforementioned signal conditioning means and the signal processor, i.e., elements 15, 18, 22 and 20, can take on a configuration as described below by reference to FIGS. 10–11. The description which follows is excerpted from the aforementioned British patent specification No. 8620239.

Figure 6:
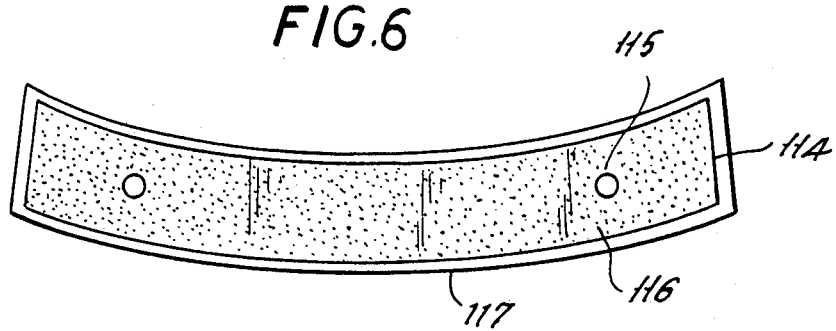
FIGS. 6 and 7 depict a sensor configuration suitable for use with the present invention.
Figure 7:
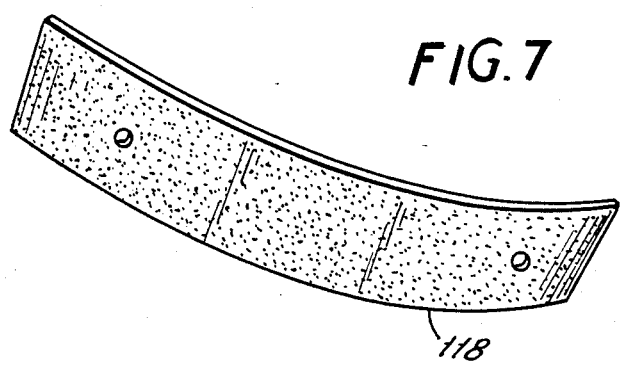
Figure 9:
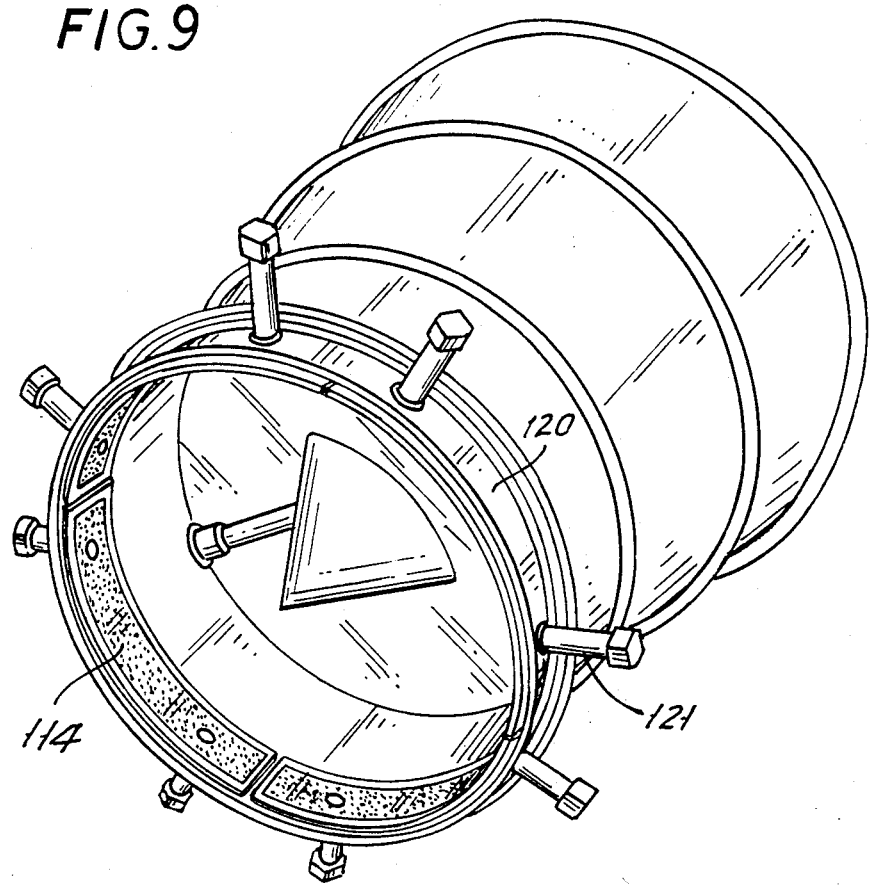
FIG. 9 is a perspective of a plurality of sensors arranged around the exhaust of a jet engine.

A typical series of probes as arranged in the exhaust gas duct of a jet engine is shown in FIG. 9 and two different perspective views of an individual probe are shown in FIGS. 6 and 7. In the particular configuration shown in FIG. 9, four segmental probes are employed to define a segmented rig sensor in the engine's exhaust duct 100. Each probe comprises an arcuate plate 114 having a pair of arcuately spaced holes 115. The face 116 of plate 114 is polished to provide a charge receiving surface and the periphery 117 and the back 118 (see FIG. 7) are covered with a coating of a ceramic, electrically insulating material.

Figure 8:
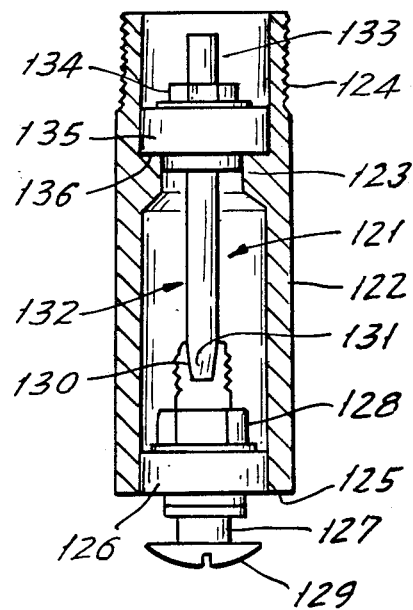
FIG. 8 shows the manner of affixing a sensor to the casing of a jet engine.

Each plate 114 is secured to the engine casing 120 by means of a securing stud assembly 121. The securing stud assembly is shown in FIG. 8 and comprises a generally cylindrical sleeve 122 which defines on its internal surface towards a first end 124 thereof a constriction 123. The external surface of the first end 124 is threaded and the second end 125 of stud assembly 121 is provided with an annular recess (not shown). The second end is adapted to accommodate an insulating member 126 formed of a ceramic material and having a central bore arranged to accommodate a metal screw 127 which is secured by nut 128 to the ceramic member 126. Screw 127 is provided with an enlarged slot 130 at its threaded end and is adapted to receive a flattened portion 131 of a stud 132. The stud 132 is generally cylindrical and is threaded at its first end 133. The first end 133 is arranged to be engaged by nut 134 which serves to clamp a further ceramic block 135 between the shoulder 136 defined by constriction 123 against ceramic member 126. The head 129 of bolt 127 serves to retain plate 114 in closely spaced relationship with the casing, but insulated therefrom while the bolt 127 and its associated stud 132 serves to provide a means of electrical connection to the face 116 of plate 114 whereby the end 133 can be electrically connected to a conductor for connection to detection sensing and analytical equipment.

The ring probes may also be used in conjunction with rod probes which are provided in the turbo fan casing for analysis of any debris present within the turbine casing itself.

Figure 10:
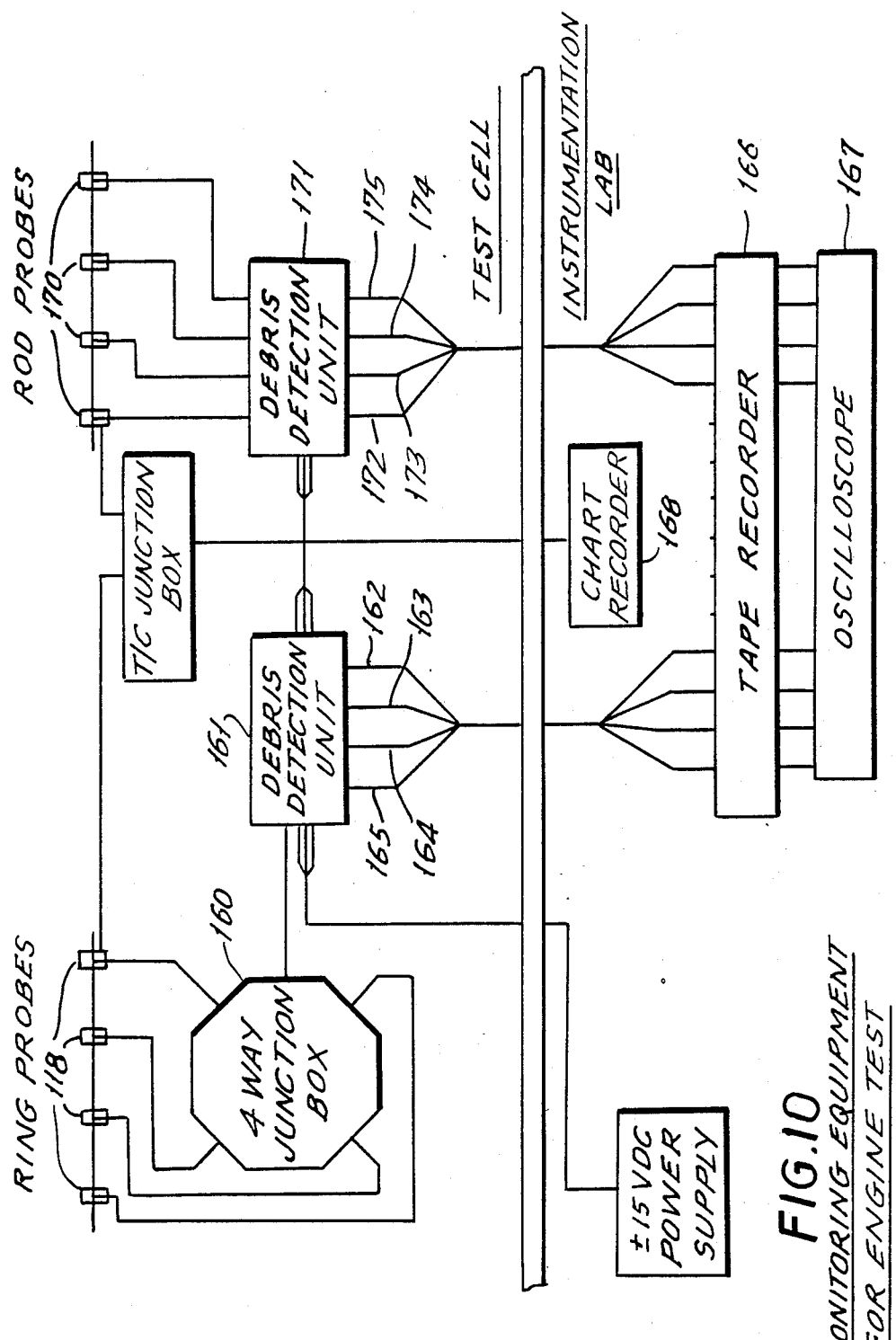
FIG. 10 is a block diagram of a sensing circuit in accordance with the present invention.

As shown in FIG. 10, the probes 118 are connected via a four way junction box 160 to supply signals to a debris detection unit 161. The debris detection unit has a channel corresponding to each ring probe and provides four outputs 162, 163, 164 and 165 each of which are connected to a tape recorder 166 and subsequently to an oscilloscope 167 to provide a visual indication of the output of the components. The debris detection unit also provides an output to a chart recorder 168.

Rod probes 170 are also connected to a debris detection unit 171 and the various outputs 172, 173, 174 and 175 are connected to tape recorder 166 and 167 and are switchable to chart recorder 168.

Figure 11:
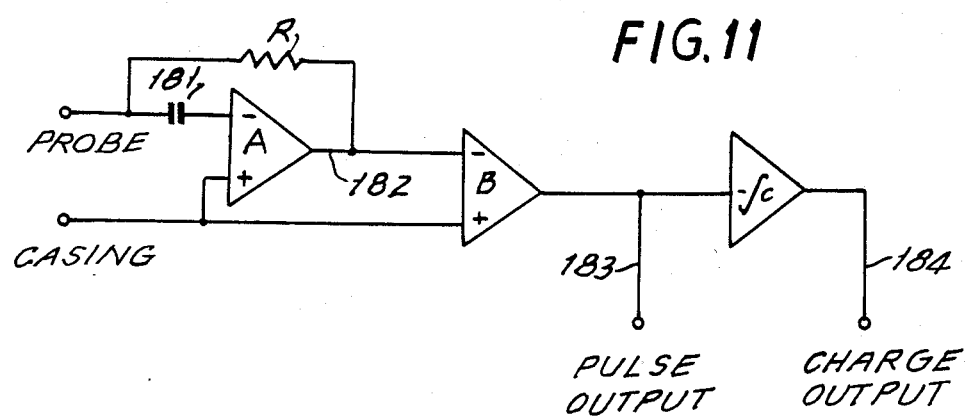
FIG. 11 is a block diagram of a circuit relevant to the block diagram of FIG. 10.

The debris detection unit 162 is shown in greater detail in FIG. 11 of the accompanying drawings and comprises a current input (transresistance) amplifier A which is an AC coupled amplifier with the gain set by resistor R. (Different types of probe installation require different settings of R) and the probe signal is AC coupled via capacitor 181 to the inverting input (−) of the amplifier A. The non-inverting terminal is connected to the engine casing. The output signal at 182 passes to the input to a differential amplifier B which removes common mode signal present between the engine casing and the equipment earth. The output from the differential amplifier B is a signal representing the rate at which the charge enters or leaves the probe region. This pulse signal is passed to a pulse outlet socket 183 for subsequent processing or tape recording. The pulse signal may also be passed to an integrating stage C, which for a ring probe, the time integral of the pulse signal represents the amount of charge inside the probe. This signal is available via a further output 184 as a charge output. While this signal does not have the same physical significance for rod and ring probes, the low pass filtering action for the integrator aids noise and interference removal.

The integrator C is selectable between 1 and 10 seconds and this provides a smoothing charge output which can be separately monitored.

I claim:

1. An apparatus for monitoring the intake of foreign bodies into a gas turbine engine, the apparatus comprising:
    at least one sensor located at or near the intake of an engine, said at least one sensor being effective to sense the passage of electrostatic charge associated with said foreign bodies adjacent said at least one sensor and for producing a signal indicative of the passage of said electrostatic charge; and
    signal conditioning means coupled to said at least one sensor and effective for conditioning said signal produced by said at least one sensor.

2. The apparatus of claim 1, wherein said at least one sensor comprises a plurality of electrically discrete sensor elements disposed in a ring about the intake of the engine, said signal conditioning means comprising a plurality of signal conditioning circuits, and each said sensor element being coupled to a respective one of said signal conditioning circuits for conditioning signals thereof.

3. The apparatus of claim 1, wherein the engine comprises a by-pass passage and further including additional sensors disposed in the by-pass passage whereby electrostatic activity in the by-pass passage can be monitored.

4. The apparatus of claim 2, wherein said signal conditioning means are effective for producing conditioned outputs and further including signal processing means, responsive to the conditioned outputs and effective to identify from said outputs events occurring within the engine, an event signifying the ingestion into the engine of a foreign body.

5. The apparatus of claim 1, wherein the engine includes an exhaust duct and including further sensors at the exhaust duct.

6. The apparatus of claim 5, wherein said conditioning means is effective for producing conditioned outputs and further including signal processing means for monitoring the conditioned outputs and for distinguishing between events occurring within the engine as a result of normal engine running and events occurring as a result of debris being ingested into the engine.

7. The apparatus of claim 1, further including signal processing means for processing signals originating in the at least one sensor and including means for measuring a rate of change of said signals.

8. The apparatus of claim 1, further including signal processing means for processing signals originating in the at least one sensor and including means for measuring the magnitude of said charge.

9. The apparatus of claim 1, wherein said at least on sensor comprises a single ring sensor and a plurality of arcuate sensors.

* * * * *